US009662400B2

(12) United States Patent
Smith et al.

(10) Patent No.: US 9,662,400 B2
(45) Date of Patent: *May 30, 2017

(54) METHODS FOR PRODUCING A BIODEGRADABLE CHITOSAN COMPOSITION AND USES THEREOF

(71) Applicant: University of Memphis Research Foundation, Memphis, TN (US)

(72) Inventors: James Keaton Smith, Memphis, TN (US); Ashley C. Parker, Memphis, TN (US); Jessica A. Jennings, Memphis, TN (US); Benjamin T. Reves, Memphis, TN (US); Warren O. Haggard, Bartlett, TN (US)

(73) Assignee: The University of Memphis Research Foundation, Memphis, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/771,617

(22) PCT Filed: Mar. 14, 2013

(86) PCT No.: PCT/US2013/031622
§ 371 (c)(1),
(2) Date: Aug. 31, 2015

(87) PCT Pub. No.: WO2014/142915
PCT Pub. Date: Sep. 18, 2014

(65) Prior Publication Data
US 2016/0000924 A1 Jan. 7, 2016

(51) Int. Cl.
| | |
|---|---|
| *A61K 47/36* | (2006.01) |
| *A61K 38/14* | (2006.01) |
| *A61K 38/12* | (2006.01) |
| *A61K 31/7036* | (2006.01) |
| *A61L 15/28* | (2006.01) |
| *C08B 37/08* | (2006.01) |
| *C08L 5/08* | (2006.01) |
| *A61L 27/20* | (2006.01) |
| *A61L 27/54* | (2006.01) |
| *A61L 27/56* | (2006.01) |
| *A61L 15/42* | (2006.01) |
| *A61L 15/46* | (2006.01) |
| *A61K 9/19* | (2006.01) |
| *A61K 9/70* | (2006.01) |
| *A61L 17/10* | (2006.01) |
| *A61K 38/00* | (2006.01) |

(52) U.S. Cl.
CPC ........... *A61K 47/36* (2013.01); *A61K 9/19* (2013.01); *A61K 9/70* (2013.01); *A61K 31/7036* (2013.01); *A61K 38/12* (2013.01); *A61K 38/14* (2013.01); *A61L 15/28* (2013.01); *A61L 15/425* (2013.01); *A61L 15/46* (2013.01); *A61L 17/10* (2013.01); *A61L 27/20* (2013.01); *A61L 27/54* (2013.01); *A61L 27/56* (2013.01); *C08B 37/003* (2013.01); *C08L 5/08* (2013.01); *A61K 38/00* (2013.01); *A61L 2300/404* (2013.01)

(58) Field of Classification Search
CPC ...... A61K 47/36; A61K 31/00; A61K 9/7007; A61K 9/0024; A61L 15/28; A61L 27/20; A61L 27/58; A61L 31/042; C08B 37/003
USPC ................. 514/23, 40, 777; 536/20
See application file for complete search history.

(56) References Cited

U.S. PATENT DOCUMENTS

| | | | |
|---|---|---|---|
| 4,895,724 A * | 1/1990 | Cardinal | A61K 9/0024 424/278.1 |
| 5,541,233 A | 7/1996 | Roenigk | |
| 5,958,443 A | 9/1999 | Viegas et al. | |
| 6,699,287 B2 | 3/2004 | Son et al. | |
| 6,989,157 B2 | 1/2006 | Gillis et al. | |
| 7,371,403 B2 | 5/2008 | McCarthy et al. | |
| 2003/0015825 A1 | 1/2003 | Sugie et al. | |
| 2003/0206958 A1 | 11/2003 | Cattaneo et al. | |
| 2007/0059473 A1 | 3/2007 | Yamazaki et al. | |
| 2009/0004276 A1 | 1/2009 | Ben-Shalom et al. | |
| 2009/0075383 A1 | 3/2009 | Buschmann et al. | |
| 2012/0149659 A1 | 6/2012 | Haggard et al. | |

FOREIGN PATENT DOCUMENTS

| | | |
|---|---|---|
| EP | 1 308177 | 5/2003 |
| JP | 02-268766 | 11/1990 |
| JP | 2003/511120 | 3/2003 |
| JP | 2004/231604 | 8/2004 |
| JP | 2006/347999 | 6/2005 |
| JP | 2006/516988 | 7/2006 |
| JP | 2008-110207 | 5/2008 |
| JP | 2008/161502 | 7/2008 |
| JP | 2008/527033 | 7/2008 |
| KR | 10-2002-0017552 | 3/2002 |
| KR | 1020020017552 A | 3/2002 |
| KR | 1020040090033 A | 10/2004 |
| KR | 2007 0118730 A | 12/2007 |

(Continued)

OTHER PUBLICATIONS

The Merck Manual 1992, pp. 183-189.*
Parker et al, J. Biomedical Materials Research B: Applied Biomaterials, 2013, 101b(1), 110-123.*
Smith, J.K. et al., "Antibiotic-loaded chitosan film for infection prevention: A preliminary in vitro characterization," Journal of Biomedical Materials Research Part B: Applied Biomaterials, 2010, vol. 94B, pp. 203-211 (see abstract and p. 204).
Parker, A.C. et al., "Preliminary investigation of crosslinked chitosan sponges for tailorable drug delivery and infection control," Journal of Biomedical Materials Research Part B: Applied Biomaterials, Sep. 21, 2012 (E-pub.), vol. 101B, pp. 110-123, See abstract: and pp. 111 and 112.

(Continued)

*Primary Examiner* — Ganapathy Krishnan
(74) *Attorney, Agent, or Firm* — Melissa Hunter-Ensor; Elbert Chiang; Greenberg Traurig, LLP

(57) ABSTRACT

The invention provides improved methods for generating biodegradable chitosan compositions, and therapeutic methods of using such compositions to deliver therapeutic agents.

17 Claims, 3 Drawing Sheets

(56) References Cited

FOREIGN PATENT DOCUMENTS

| WO | 01/41820 A1 | 6/2001 |
| WO | 2004/078063 A2 | 9/2004 |
| WO | 2008/157318 A2 | 12/2008 |
| WO | 2009/056602 A1 | 5/2009 |

OTHER PUBLICATIONS

Notification of Transmittal of the International Search Report and the Written Opinion of the International Searching Authority in corresponding PCT/US2013/031622, dated Nov. 26, 2013 (14 pages).
Niekraszewicz; "Chitosan Medical Dressings", Institute of Chemical Fibres ul. M. Sklodowskiej-Curie 19/27, 90-570 Lodz, Poland, Fibres & Textiles in Eastern Europe Jan./Dec. 2005, vol. 13, No. 6 (54).
Bonferoni et al., "Chitosan Gels for the Vaginal Delivery of Lactic Acid: Relevance of Formulation Parameters to Mucoadhesion and Release Mechanisms", AAPS PharmSciTech 2006; 7 (4) Article 104 (http://www.aapspharmscitech.org).
International Search Report issued for International Application No. PCT/US2010/027481, completed Oct. 28, 2010 and mailed Nov. 2, 2010.
Antonov et al., "Study of Wound Healing Properties of Chitosan", Russian Agricultural Sciences, vol. 34, No. 6, pp. 426-427 (2008).
Kiang et al., "The effect of the degree of chitosan deacetylation on the efficiency of gene transfection", Biomaterials, vol. 25, pp. 5293-5301 (2004).
European Search Report issued in European Patent Application No. 10753982.7 on Aug. 6, 2013.
JP Office Action, issued in JP App No. 2012-500887 (translation), mailed Jan. 7, 2015.

* cited by examiner

METHODS FOR PRODUCING A BIODEGRADABLE CHITOSAN COMPOSITION AND USES THEREOF

STATEMENT OF RIGHTS TO INVENTIONS MADE UNDER FEDERALLY SPONSORED RESEARCH

This work was supported by the following grants from the U.S. Department of the Army: USAMRAA Grant No. W81XWH-12-2-0020. The government has certain rights in the invention.

This application is the U.S. national phase application, pursuant to 35 U.S.C. §371, of PCT international application Ser. No. PCT/US2013/031622, filed Mar. 14, 2013, designating the United States and published in English. The entire contents of the aforementioned patent applications are incorporated herein by this reference.

BACKGROUND OF THE INVENTION

The skin serves as an important barrier to infection. Any trauma that breaks the skin creates an opportunity for pathogen entry and infection. Open fractures are ideal sites for infection. Surgical site infections in closed fractures range from 3.6-8.1%. In contrast, surgical site infections in open fractures range from 17.5-21.2%. Pathogens present at the site of an open fracture may create not only local infections, but can also cause serious infections in the bone and associated tissues. Complex open wounds are also prone to infection with a number of bacteria. The type of bacteria infecting the wound typically varies depending on the cause of the trauma. To reduce the risk of infection, the current standard of care involves debridement, irrigation, and systemic antibiotic therapy. Even with aggressive therapies and systemic antibiotic treatment, infections remain a significant source of morbidity and mortality. Tissues compromised by trauma and infection often have reduced vascularization, which limits the delivery of circulating therapeutics. Increased concentrations of systemic antibiotics are usually required to compensate for poor circulation in the damaged tissue. Antibiotic toxicity and systemic side effects are serious problems associated with this course of therapy. Infections following surgery, drug side effects, and related complications can significantly increase hospital stays and result in adverse outcomes. Because current methods for treating or preventing infection, particularly infections related to open fractures, are inadequate, improved compositions and methods for providing agents to prevent or treat an infection at a site of trauma are urgently required.

SUMMARY OF THE INVENTION

As described below, the invention features improved methods for generating biodegradable chitosan compositions, and therapeutic methods of using such compositions to deliver therapeutic agents. In particular, the invention provides for methods of generating chitosan sponges where the methods include a "buffering step."

In one aspect, the invention provides a method for producing a biodegradable chitosan composition having a desired biodegradation profile, the method involving
(a) dissolving chitosan having a degree of deacetylation of at least about 51% in one or more acids in a solvent, wherein the acid and solvent are selected to produce a chitosan that biodegrades over at least about 1-30 days in vivo; and
(b) forming the chitosan into a desired shape under conditions that reduce the water content by about 10%-100%.
(c) neutralizing the chitosan composition by contacting the composition with water, a neutral, or a basic solution, wherein the water, neutral, or basic solution is selected to modulate a physical-mechanical property of the chitosan; and
(d) contacting the chitosan composition with an acid buffer wash, thereby producing a biodegradable chitosan composition.

In another aspect, the invention provides a chitosan composition produced by the method of the previous aspect, or any other method described herein.

In another aspect, the invention provides a wound management device containing a chitosan composition produced by the method described in the previous aspects. In one embodiment, the device contains an effective amount of a therapeutic agent. In another embodiment, the effective amount of the agent is sufficient to reduce the survival or proliferation of a bacterial cell. In still another embodiment, the agent is an antibiotic selected from the group consisting of daptomycin, vancomycin, and amikacin. In still another embodiment, the agent is any one or more of growth factor, anti-inflammatory, hemostatic, and anti-thrombotic. In still another embodiment, the agent is an anti-bacterial, anti-viral, or anti-fungal agent.

In another aspect, the invention provides a method for treating or preventing an infection in a subject at a site of trauma, the method involves contacting the site with a chitosan composition or a wound management device of any previous aspect. In other embodiments, the method further involves irrigating and debriding the site of trauma. In other embodiments, the composition or device contains an agent that is any one or more of antimicrobial agent, growth factor, anti-inflammatory, hemostatic agent, and anti-thrombotic. In still other embodiments, the trauma is a fracture, open fracture, wound, complex wound, and surgical site.

In another aspect, the invention provides a kit containing a chitosan composition of any previous aspect for use in treating a trauma site or delivering an agent. In one embodiment, the chitosan composition or device is in the form of a plug, mesh, strip, suture, dressing, sponge, film, hydrogel, or combinations thereof. In another embodiment, the chitosan composition or device contains an agent selected from the group consisting of antimicrobial agent, growth factor, anti-inflammatory, clot promoting agent, and anti-thrombotic.

In various embodiments of the above aspects or any aspect of the invention delineated herein the buffer has a pH between 2.5 and 6.5 or between 5 and 6 (e.g., 5.1, 5.2, 5.3, 5.4, 5.5, 5.6, 5.7, 5.8, 5.9, and 6.0). In other embodiments, the buffer is any one or more acetate, bicarbonate, carbonate, citrate, formate, glycine, malate, maleate, 2-(N-morpholino) ethanesulfonate, phosphate, proprionate, and succinate. In one preferred embodiment, the buffer is an acetate buffer. In other embodiments, the sponge is contacted with the acid buffer wash for between about 30 seconds and 12 hours (e.g., 1, 3, 5, 10, 15, 30, 45, 60 minutes, 1, 3, 5, 10, and 12 hours). In still another embodiment, the sponge is contacted with the acid buffer wash having a concentration between about 0.05 and 2.0 molar. In still another embodiment, a 0.25 M acetate buffer is used. In yet other embodiments, the sponge degrades by at least about 20%, 30%, 40%, 50%, 60% or more in an in vitro degradation assay in about 10-days. In yet other embodiments, the sponge degrades by at least about 20%, 30%, 40%, 50%, 60% or more in vivo in about 10-days. In still other embodiments, the method further involves (d) incorporating an effective amount of at least one agent into the chitosan composition at a point of care. In still other embodiments, the acid buffer type, buffer, concentration, buffer pH, and buffer soaking time are varied to optimize the degradation of the sponge. In yet other embodiments, the chitosan composition is a wound management device. In still other embodiments, the agent is an antimicrobial. In yet other embodiments, the chitosan is treated with an acid solvent that is any one or more of acetic, citric, oxalic, propionic, ascorbic, hydrochloric, formic, salicylic and lactic acids. In yet other embodiments, the acid solvent contains lactic acid and/or acetic acid. In yet other embodiments, at least about 30, 40, 50 or 60% of the chitosan composition biodegrades over at least about three-five days when implanted in a subject. In still other embodiments, the chitosan composition is molded to form a plug, mesh, strip, suture, dressing, sponge, or film.

The invention provides compositions featuring chitosan and methods for using such compositions for the local delivery of biologically active agents to an open fracture, complex wound or other site of infection. Compositions and articles defined by the invention were isolated or otherwise manufactured in connection with the examples provided below. Other features and advantages of the invention will be apparent from the detailed description, and from the claims.

DEFINITIONS

By "chitosan" is meant a chitin-derived polymer that is at least 20% deacetylated. Preferably, chitosan is at least about 50% deacetylated. Chitin is a linear polysaccharide consisting of (1-4)-linked 2-acetamido-2-deoxy-b-D-glucopyranose. Chitosan is a linear polysaccharide consisting of (1-4)-linked 2-amino-2-deoxy-b-D-glucopyranose.

By "composite" is meant a mixture of materials. In one embodiment, a composite comprises sponge fragments dispersed within a hydrogel.

By "acid treated chitosan" is meant chitosan that is solubilized in an acidic solution.

By "degrades" is meant physically or chemically breaks down in whole or in part. Preferably, the degradation represents a physical reduction in the mass by at least about 10%, 25%, 50%, 75%, 80%, 85%, 90%, 95% or 100%.

By "film" is meant a thin layer of material.

By "long term release" is meant elution of an agent over the course of twenty-four to seventy two hours or longer.

By "sponge" is meant a three-dimensional porous matrix.

By "wound management device" or "wound healing device" is meant any material used to protect or promote healing at a site of trauma.

By "agent" is meant any small compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) as detected by standard art known methods such as those described herein.

By "analog" is meant a molecule that is not identical, but has analogous functional or structural features. For example, a chitosan analog retains the biological activity of a corresponding reference chitosan polymer (e.g., manufactured chitosan), while having certain biochemical modifications that enhance the analog's function relative to a reference chitosan polymer. Such biochemical modifications could increase the analog's ability to be degraded, to uptake or elute a therapeutic agent, or to increase or decrease mechanical strength.

By "antimicrobial" is meant an agent that inhibits or stabilizes the proliferation or survival of a microbe. In one embodiment, a bacteriostatic agent is an antimicrobial. In other embodiments, any agent that kills a microbe (e.g., bacterium, fungus, virus) is an antimicrobial.

By "anti-inflammatory" is meant an agent that reduces the severity or symptoms of an inflammatory reaction in a tissue. An inflammatory reaction within tissue is generally characterized by leukocyte infiltration, edema, redness, pain, and/or neovascularization. Inflammation can also be measured by analyzing levels of cytokines or any other inflammatory marker.

By "biodegradable" is meant susceptible to breakdown by biological activity. For example, biodegradable chitosan compositions are susceptible to breakdown by enzymes present in vivo (e.g., lysozyme, N-acetyl-o-glucosaminidase and lipases). Degradation of a chitosan composition of the invention need not be complete. A chitosan composition of the invention may be degraded, for example, by the cleavage of one or more chemical bonds (e.g., glycosidic bonds). Advantageously, degradation is by at least about 20, 30, 40, 50, 60, 70, 80, 90, 95% or more over 3-5, 5-7, 7-9, 10-15, or 15-30 days.

By "clinician" is meant any healthcare provider. Exemplary clinicians include, but are not limited to, doctors, veterinarians, osteopaths, physician's assistants, emergency medical technicians, medics, nurse practitioners, and nurses.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "customize" is meant tailor to suit the needs of a particular subject.

By "degradation rate" is meant the time required to substantially degrade the composition. A composition is substantially degraded where at least about 20%, 30%, 40%, 50%, 60%, 75%, 85%, 90%, 95% or more has been degraded. Methods for measuring degradation of chitosan are known in the art and include measuring the amount of a sponge, film, composite or other composition of the invention that remains following implantation in a subject or following in vitro exposure to an enzyme having chitosan-degrading activity.

By "disease" is meant any condition or disorder that damages or interferes with the normal function of a cell, tissue, or organ. In one example, a disease is a bacterial or other infection present in a wound site. In another embodiment, a disease is sepsis.

By "effective amount" is meant the amount of an agent required to ameliorate the symptoms of a disease relative to an untreated patient. The effective amount of active agent(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "elution rate" is meant the time required for an agent to be substantially released from a composition. Elution can be measured by determining how much of an agent remains within the composition or by measuring how much of an agent has been released into the composition's surroundings. Elution may be partial (10%, 25%, 50%, 75%, 80%, 85%, 90%, 95% or more) or complete. In one preferred embodiment, the agent continues to be released at an effective level for at least about 3, 4, 5, 6, 7, 8, 9, or 10 days.

The invention provides a number of targets that are useful for the development of highly specific drugs to treat or a disorder characterized by the methods delineated herein. In addition, the methods of the invention provide a *facile* means to identify therapies that are safe for use in subjects. In addition, the methods of the invention provide a route for analyzing virtually any number of compounds for effects on wound healing or pathogen infection described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Chitosan compositions are useful for the delivery of polynucleotides, such as inhibitory nucleic acid molecules, useful for the treatment or prevention of pathogen infection and related disease. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

By "infection" is meant the presence of one or more pathogens in a tissue or organ of a host. An infection includes the proliferation of a microbe (e.g., bacteria, viruses, fungi) within a tissue of a subject at a site of trauma.

By "marker" is meant any protein or polynucleotide having an alteration in expression level or activity that is associated with a disease or disorder.

By "modulate" is meant alter (increase or decrease). Such alterations are detected by standard art known methods such as those described herein.

As used herein, "obtaining" as in "obtaining an agent" includes synthesizing, purchasing, or otherwise acquiring the agent.

By "physical interaction" is meant an association that does not require covalent bonding. In one embodiment, a physical interaction includes incorporation into a chitosan composition of the invention.

By "point of treatment" is meant the site where healthcare is delivered. A "point of treatment" includes, but is not limited to, a surgical suite, physician's office, clinic, or hospital.

By "polymer" is meant a natural or synthetic organic molecule formed by combining smaller molecules.

By "profile" is meant a set of characteristics that define a composition or process. For example, a "biodegradation profile" refers to the biodegradation characteristics of a composition. In another example, an "elution profile" refers to elution characteristics of a composition.

By "prosthetic device" is meant an implanted medical device that substitutes for or supplements a missing or defective part of the body.

By "small molecule" is meant any chemical compound.

By "trauma" is meant any injury that damages a tissue or organ of a subject. The injury need not be severe. Therefore, a trauma includes any injury that breaks the skin.

By "modulation" is meant any alteration (e.g., increase or decrease) in a biological function or activity.

By "subject" is meant a mammal, including, but not limited to, a human or non-human mammal, such as a bovine, equine, canine, ovine, or feline.

By "uniform degree of deacetylation" refers to a chitosan composition made from a single type of chitosan, (e.g., 61 degrees of deacetylation (DDA), 71DDA, or 81DDA). In one embodiment, a chitosan composition having a uniform degree of deacetylation excludes chitosan compositions having a combination of types of chitosans, where the chitosans have different degrees of deacetylation.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reference" is meant a standard or control condition.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

DETAILED DESCRIPTION OF THE INVENTION

Figure 1:
FIG. 1 shows a neutralized, large chitosan sponges (approximately 5"×5") in the water wash step (Step 5).

As described below, the present invention features improved methods for producing biodegradable chitosan compositions (e.g., solids, sponges, films, hydrogels, composites) that provide for the local delivery of biologically active agents and methods of using such compositions to treat or prevent an infection or promote healing.

The invention is based, at least in part, on the discovery that adding a "buffering step" to the method of generating a chitosan sponge provides the ability to better control the chitosan sponge degradation. Briefly, the improved method involves dissolving chitosan in a weak organic acid aqueous solution, freezing the resulting chitosan and acid solution; lyophilizing the frozen, solid chitosan solution, removing the water; and then neutralizing the resulting dehydrated, acidic chitosan "sponge" by hydrating it in an excess concentration and volume of sodium hydroxide aqueous solution. The residual acidic and basic products were then washed away using a copious amount ultrapure water.

In a "buffering step," the hydrated, neutralized chitosan sponge is soaked in a 0.25M acetate buffer solution at pH 5.6 for thirty minutes.

Following this step, the excess liquid is removed from the sponge, which is then frozen, lyophilized and the final buffered chitosan sponge may be stored in a low humidity environment.

This method provides a reproducibly and uniformly degradable chitosan sponge. Additionally, it allows for the degradation process to be controlled by varying the acid buffer type, buffer concentration, buffer pH, and buffer soaking time to yield a chitosan sponge having a desired degradation profile.

Chitosan

Chitosan is a naturally occurring linear polysaccharide composed of randomly distributed β-(1-4)-2-amino-2-D-glucosamine (deacetylated) and β-(1-4)-2-acetamido-2-D-glucoseamine (acetylated) units. Chitosan is derived from chitin, a naturally occurring polymer. Chitin is a white, hard, inelastic, nitrogenous polysaccharide isolated from fungi, mollusks, or from the exoskeletons of arthropods (e.g., crustaceans, insects). The major procedure for obtaining chitosan is the alkaline deacetylation of chitin with strong alkaline solution. Generally, the raw material is crushed, washed with water or detergent, and ground into small pieces. After grinding, the raw material is treated with alkali and acid to isolate the polymer from the raw crushed material. The polymer is then deacetylated by treatment with alkali. Chitin and chitosan differ in their degrees of deacetylation (DDA). Chitin has a degree of deacetylation of 0% while pure chitosan has a degree of deacetylation of 100%. Typically, when the degree of deacetylation is greater than about 50% the polymer is referred to as chitosan.

Chitosan is a cationic weak base that is substantially insoluble in water and organic solvents. Typically, chitosan is fairly soluble in dilute acid solutions, such as acetic, citric, oxalic, proprionic, ascorbic, hydrochloric, formic, and lactic acids, as well as other organic and inorganic acids. Chitosan's charge gives it bioadhesive properties that allow it to bind to negatively charged surfaces, such as biological tissues present at a site of trauma or negatively charged implanted devices. Chitosan's degree of deacetylation affects it resorption. Chitosan compositions having a 50% degree of deacetylation are highly degradable in vivo. As the degree of deacetylation increases, chitosan becomes increasingly resistant to degradation. Chitosan compositions having a degree of deacetylation that is higher than 95% degrade slowly over weeks or months. In the body chitosan is degraded by lysozyme, N-acetyl-o-glucosaminidase and lipases. Lysozyme degrades chitosan by cleaving the glycosidic bonds between the repeating chitosan units. The byproducts of chitosan degradation are saccharides and glucosamines that are gradually absorbed by the human body. Therefore, when chitosan is used for the local delivery of therapeutic or prophylactic agents, no secondary removal operation is required.

The present invention provides improved methods for generating biodegradable composition. In particular, such methods include a buffering step where the buffer has a pH between 2.5 and 6.5 (e.g., 2.5, 3.0, 4.0, 5.0, 5.1, 5.2, 5.3, 5.4, 5.5, 5.6, 5.7, 5.8, 5.9, and 6.0). In certain embodiments, the buffer is sodium or potassium acetate, bicarbonate, carbonate, citrate, formate, glycine, malate, maleate, 2-(N-morpholino)ethanesulfonate, phosphate, proprionate, or succinate buffer. The buffering treatment is optimized to a desired degradation profile. Time of buffering treatment can be from as little as 30 seconds to as long as 12 hours (e.g., 1, 3, 5, 10, 15, 30, 45, 60 minutes, 1, 3, 5, 10, 12 hours). The concentration of the buffer may be varied between about 0.05 and 2.0 molar. Preferably, such variables are adjusted such that the sponge degrades by at least about 20%, 30%, 40%, 50%, 60% or more in 3, 5, 7 or 10-days.

As reported herein, chitosan compositions (e.g., solids, sponges, films, hydrogels, composites) can be loaded with a biologically active agent at the site of care (e.g., in a surgical suite, clinic, or physician's office, trauma site, battlefield). This property allows the clinician to tailor the antibiotics or other agents used to load the chitosan wound management device to suit the needs of a particular patient. In one embodiment, the degree of deacetylation is adjusted to provide chitosan compositions that degrade in as little as about twenty-four, thirty-six, forty-eight, or seventy two hours or that are maintained for a longer period of time (e.g., 4, 5, 6, 7, 8, 9, 10 days). In other embodiments, chitosan compositions of the invention are maintained in the body for at least about two-six weeks or more (e.g., 2, 3, 4, 5, 6 weeks, two, three or four months). In still other embodiments, chitosan compositions of the invention enhance blood clotting in a wound or other site of trauma (hemostasis). In other embodiments, the chitosan compositions are loaded with therapeutic or prophylactic agents that are clinician selected and that are delivered over at least about 1, 2, 3, 4, 5, 6, 7, 8, 9, or 10 days or for longer periods.

Antimicrobial Agents

*Staphylococcus aureus, staphylococcus epidermidis*, and *Pseudomonas aeruginosa* are pathogens that are commonly present at musculoskeletal wound sites. *S. aureus* is one cause of osteomyelitis and nongonococcal bacterial arthritis, and is often associated with prosthetic joint infection. The invention provides chitosan compositions useful in treating or preventing infection in a wound, complex wound, open fraction, or other site of trauma. Any antimicrobial agent known in the art can be used in the chitosan compositions of the invention at concentrations generally used for such agents.

Antimicrobial agents useful in chitosan compositions of the invention include but are not limited to antibacterials, antifungals, and antivirals. An antimicrobial agent as used herein is an agent that reduces or stabilizes the survival, growth, or proliferation of a pathogen. Antimicrobial agents include but are not limited to Aztreonam; Chlorhexidine Gluconate; Imidurea; Lycetamine; Nibroxane; Pirazmonam Sodium; Propionic Acid; Pyrithione Sodium; Sanguinarium Chloride; Tigemonam Dicholine; Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefinenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride, Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Trometamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin lydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacil; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz: Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium: Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin; Difloxacin Hydrochloride; Lauryl Isoquinolinium Bromide; Moxalactam Disodium; Ornidazole; Pentisomicin; and Sarafloxacin Hydrochloride. In particular embodiments, a chitosan composition comprises daptomycin.

In one preferred embodiment, a chitosan composition of the invention comprises an agent that treats a multidrug resistant bacteria. In one approach, linezolid may be used to treat multi-drug resistant Gram positive bacteria. Linezolid is commercially available under the trade name Zyvox (Pfizer).

In other embodiments, a chitosan composition comprises one or more of the following: Benzalkonium Chloride, Cetylpyridinium Chloride, and Chlorhexidine Digluconate. In still other embodiments, a chitosan composition comprises one or more of antimicrobials: Polyhexamethylene Biguanide, Octenidine Dihydrochloride, Mild Silver Protein, Povidone Iodine (solution or ointment), Silver Nitrate, Silver Sulfadiazine, Triclosan, Cetalkonium Chloride, Myristalkonium Chloride, Tigecycline, Lactoferrin, Quinupristin/dalfopristin, Linezolid, Dalbavancin, Doripenem, Imipenem, Meropenem, and Iclaprim.

In still other embodiments, the chitosan composition comprises an essential oil having antimicrobial properties. Exemplary essential oils include Oregano oil, tea tree oil, mint oil, sandalwood oil, clove oil, nigella sativa oil, onion oil, leleshwa oil, lavender oil, lemon oil, lemon myrtle oil, neem oil, garlic, eucalyptus oil, peppermint oil, cinnamon oil, and thyme oil.

In still other embodiments, the antimicrobial is a fatty acid (e.g., Cis-2-Decenoic Acid).

Antivirals are agents capable of inhibiting the replication of viruses. Examples of anti-viral agents include but are not limited to 1,-D-ribofuranosyl-1,2,4-triazole-3 carboxamide, 9-2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

Antifungal agents useful in chitosan compositions of the invention include fungicidal and fungistatic agents such as, for example, benzoic acid, undecylenic alkanolamide, ciclopirox olamine, polyenes, imidazoles, allylamine, thicarbamates, amphotericin B, butylparaben, clindamycin, econaxole, fluconazole, flucytosine, griseofulvin, nystatin, ketoconazole, and voriconazole. In one preferred embodiment, the antifungal is amphotericin B.

In one embodiment, the invention provides chitosan compositions comprising a combination of one or more antimicrobials and antivirals or antifungals.

Growth Factors

Growth factors are typically polypeptides or fragments thereof that support the survival, growth, or differentiation of a cell. Such agents may be used to promote wound healing. A chitosan composition described herein can be used to deliver virtually any growth factor known in the art. Such growth factors include but are not limited to angiopoietin, acidic fibroblast growth factors (aFGF) (GenBank Accession No. NP_149127) and basic FGF (GenBank Accession No. AAA52448), bone morphogenic protein (BMP) (GenBank Accession No. BAD92827), vascular endothelial growth factor (VEGF) (GenBank Accession No. AAA35789 or NP_001020539), epidermal growth factor (EGF) (GenBank Accession No. NP_001954), transforming growth factor α (TGF-α) (GenBank Accession No. NP_003227) and transforming growth factor β (TFG-β) (GenBank Accession No. 1109243A), platelet-derived endothelial cell growth factor (PD-ECGF) (GenBank Accession No. NP_001944), platelet-derived growth factor (PDGF) (GenBank Accession No. 1109245A), tumor necrosis factor α (TNF-α) (GenBank Accession No. CAA26669), hepatocyte growth factor (HGF) (GenBank Accession No. BAA14348), insulin like growth factor (IGF) (GenBank Accession No. P08833), erythropoietin (GenBank Accession No. P01588), colony stimulating factor (CSF), macrophage-CSF (M-CSF) (GenBank Accession No. AAB59527), granulocyte/macrophage CSF (GM-CSF) (GenBank Accession No. NP_000749) and nitric oxide synthase (NOS) (GenBank Accession No. AAA36365). In one preferred embodiment, the growth factor is BMP.

Analgesics

Chitosan compositions of the invention can be used for the delivery of one or more agents that ameliorate pain, such agents include but are not limited to opioid analgesics (e.g. morphine, hydromorphone, oxymorphone, levorphanol, levallorphan, methadone, meperidine, fentanyl, codeine, dihydrocodeine, oxycodone, hydrocodone, propoxyphene, nalmefene, nalorphine, naloxone, naltrexone, buprenorphine, butorphanol, nalbuphine or pentazocine; a nonsteroidal antiinflammatory drug (NSAID) (e.g., aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac, or a pharmaceutically acceptable salt thereof; a barbiturate sedative, e.g. amobarbital, aprobarbital, butabarbital, butalbital, mephobarbital, metharbital, methohexital, pentobarbital, phenobartital, secobarbital, talbutal, theamylal or thiopental or a pharmaceutically acceptable salt thereof; a COX-2 inhibitor (e.g. celecoxib, rofecoxib or valdecoxib.

Anti-Thrombotic

Chitosan compositions of the invention are also useful for inhibiting, reducing or ameliorating clot formation. In one embodiment, a chitosan composition contains one or more anti-thrombotics (e.g., thrombin, fibrinogen, cumidin, heparin and calcium salts).

Anti-Inflammatories

In other embodiments, a chitosan composition is used to deliver an anti-inflammatory agent. Such anti-inflammatory agents include, but are not limited to, Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluoromethalone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone;

Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; and Zomepirac Sodium.

Delivery of Agents Via Chitosan Compositions

The invention provides a simple means for delivering biologically active agents (e.g., small compounds, nucleic acid molecules, polypeptides) using a chitosan composition. The chitosan composition is delivered to a subject and the biologically active agent is eluted from the composition in situ. The chitosan composition is capable of delivering a therapeutic for the treatment of a disease or disorder that requires controlled and/or localized drug delivery over some period of time (e.g., 1, 3, 5, 7 days; 2, 3, 4 weeks; 1, 2, 3, 6, 12 months). Desirably, the chitosan composition comprises an effective amount of one or more antibiotics (e.g., amikacin, daptomycin, vancomycin), growth factors that promote wound healing, small molecules, hemostatic agents (e.g., thrombin and/or fibrinogen), anti-thrombotics (e.g., heparin), or cartilage or bone repair agents. The chitosan composition are administered in the form of solids, sponges, films, hydrogels, or composites (e.g., sponge fragments in a hydrogel matrix).

Preferably, the chitosan composition comprises at least about 1 μg, 25 μg, 50 μg, 100 μg, 250 μg, 500 μg, 750 μg, 1 mg, 5 mg, 10 mg, 25 mg, 50 mg, 75 mg, 100 mg, 200 mg, 250 mg, 300 mg, 400 mg, or 500 mg of an agent (e.g., an antibiotic). In another embodiment, the composition releases at least about 1 μg, 25 μg, 50 μg, 100 μg, 250 μg, 500 μg, 750 μg, 1 mg, 5 mg, 10 mg, 25 mg, 50 mg, 75 mg, 100 mg, 200 mg, 250 mg, 300 mg, 400 mg, or 500 mg of an agent (e.g., an antibiotic) over the course of at least about 1, 2, 3, 4, 5, 6, 7, 8, 9, 10, 14, 21, 28, or 35 days. In still another embodiment, the composition comprises at least about 1 μg, 25 μg, 50 μg, 100 μg, 250 μg, 500 μg, 750 μg, 1 mg, 5 mg, 10 mg, 25 mg, 50 mg, 75 mg, 100 mg, 200 mg, 250 mg, 300 mg, 400 mg, or 500 mg of an agent (e.g., an antibiotic) per $cm^3$.

Chitosan Coatings

A chitosan composition may be included in a coating material, such as a film, that is used to coat or wrap a medical device (e.g., drug delivery or other medical device). Such coatings are used, for example, for treating or preventing a pathogen infection or for drug delivery. In orthopedics, many post-surgical infections are associated with implant materials. Patients receiving an orthopedic implants have an infection risk of about 5% for total joint replacements. Bacteria are passively adsorbed on biomaterial surfaces after implantation. The fundamental pathogenic mechanism in biomaterial-centered sepsis is microbial colonization of the biomaterials followed by adjacent damaged tissues. Patients that suffer from such infections often require the removal and replacement of the implant to eradicate the infection.

To treat or prevent an implant-associated infection a chitosan composition of the invention is applied to the medical device (e.g., implant). The chitosan composition provides for release of a therapeutic or prophylactic agent from the device. Such agents advantageously reduce the risk of infection associated with conventional implants. Such coatings can be applied to any medical device known in the art, including, but not limited to orthopedic devices (e.g., for joint implants, fracture repairs, spinal implants, screws, rods, plates); surgical devices (e.g., sutures, staples, anastomosis devices, vertebral disks, bone pins, suture anchors, hemostatic barriers, clamps, screws, plates, clips, vascular implants, tissue adhesives and sealants, tissue scaffolds); wound management devices; drug-delivering vascular stents (e.g., a balloon-expanded stents); other vascular devices (e.g., grafts, catheters, valves, artificial hearts, heart assist devices); implantable defibrillators; blood oxygenator devices (e.g., tubing, membranes); membranes; biosensors; shunts for hydrocephalus; endoscopic devices; infection control devices; dental devices (e.g., dental implants, fracture repair devices), urological devices (e.g., penile, sphincter, urethral, bladder and renal devices, and catheters); colostomy bag attachment devices; ophthalmic devices (e.g. intraocular coils/screws); glaucoma drain shunts; synthetic prostheses (e.g., breast); intraocular lenses; respiratory, peripheral cardiovascular, spinal, neurological, dental, ear/nose/throat (e.g., ear drainage tubes); renal devices; and dialysis (e.g., tubing, membranes, grafts), urinary catheters, intravenous catheters, small diameter grafts, vascular grafts, artificial lung catheters, atrial septal defect closures, electrostimulation leads for cardiac rhythm management (e.g., pacer leads), glucose sensors (long-term and short-term), degradable coronary stents (e.g., degradable, non-degradable, peripheral), blood pressure and stent graft catheters, birth control devices, prostate cancer implants, bone repair/augmentation devices, breast implants, cartilage repair devices, dental implants, implanted drug infusion tubes, intravitreal drug delivery devices, nerve regeneration conduits, oncological implants, electrostimulation leads, pain management implants, spinal/orthopedic repair devices, wound dressings, embolic protection filters, abdominal aortic aneurysm grafts, heart valves (e.g., mechanical, polymeric, tissue, percutaneous, carbon, sewing cuff), valve annuloplasty devices, mitral valve repair devices, vascular intervention devices, left ventricle assist devices, neuro aneurysm treatment coils, neurological catheters, left atrial appendage filters, hemodialysis devices, catheter cuff, anastomotic closures, vascular access catheters, cardiac sensors, uterine bleeding patches, urological catheters/stents/implants, in vitro diagnostics, aneurysm exclusion devices, and neuropatches.

Examples of other suitable devices include, but are not limited to, vena cava filters, urinary dialators, endoscopic surgical tissue extractors, atherectomy catheters, clot extraction catheters, coronary guidewires, drug infusion catheters, esophageal stents, circulatory support systems, angiographic catheters, coronary and peripheral guidewires, hemodialysis catheters, neurovascular balloon catheters, tympanostomy vent tubes, cerebro-spinal fluid shunts, defibrillator leads, percutaneous closure devices, drainage tubes, thoracic cavity suction drainage catheters, electrophysiology catheters, stroke therapy catheters, abscess drainage catheters, biliary drainage products, dialysis catheters, central venous access catheters, and parental feeding catheters.

It is noted that in other embodiments of the present invention, the chitosan composition of the present invention may self adhere to the medical device or may be adhered to the device by means other than coating materials, such as adhesives, sutures, or compression. Any suitable method know in the art may be utilized to adhere the chitosan composition to a surface. For example, the chitosan composition may be adhered to the surface by pressing the chitosan composition onto the device, wrapping the device with a chitosan film, or spraying a chitosan composition onto the device.

The chitosan compositions with biocompatible surfaces may be utilized for various medical applications including, but not limited to, drug delivery devices for the controlled release of pharmacologically active agents, including wound healing devices, such as hemostatic sponges, dressings, suture material and meshes, medical device coatings/films and other biocompatible implants. The methods of the invention would also provides for the controlled degradation of the coating to a suitable timeframe for release of active components.

Chitosan Fibers

Randomly oriented fibrous mats can be made from chitosan by electrospinning (Schiffman and Schauer, Biomacromolecules, 2007. 8(9): p. 2665-7). These fibers are typically a mean diameter of 100 nm, but the diameter of the fibers can vary widely depending upon a number of factors. Some fibers can be as large as 1 µm in diameter, and as small as 28 nm. Typically, fibrous mats have a mean diameter between 100-200 nm.

In one approach, about 7-9 wt % chitosan is dissolved in 99-100% trifluoroacetic acid. The solvent solution contains about 0-30% methylene chloride to aid in spinnability. The solution is gently mixed for 24 hours. At this point additives such as drugs, proteins, calcium phosphate salts, or other biologically active constituents can be added. The solution is loaded into a plastic 10 mL syringe. In one embodiment, a blunt 21 gauge (G) metal needle is used. In other embodiments, needle sizes range from about 16-23G. The syringe is loaded into a syringe pump and the flowrate is set for 20-30 µL/min (usually 20 µL/min) The needle is connected to the positive electrode of the power source, while the target is connected to the ground. The target can consist of a copper plate wrapped in aluminum foil, an aluminum SEM stub, or any other conductive surface. The voltage is set between 15-26 kV. The distance between the tip and the target is between about 12-25 cm. In one preferred embodiment, 15-16 cm is used. Typically, the apparatus is used inside a ventilated box within fume hood. The box protects the fibers from air currents as they are deposited on the target. Once deposited, the fiber mat can be removed from the surface and treated as follows. Typically, the fiber mat is maintained under vacuum for about 24 hours, and then the fiber mat is neutralized in 5M $Na_2CO_3$. After drying, mats are cut to any desired size and sterilized. Another method to electrospin chitosan involves using 1,1,1,3,3,3-Hexafluoroisopropanol (HFIP) as a solvent (Shin et al., J Periodontol, 2005. 76(10): p. 1778-84). One advantage is that there is no need to neutralize the mat. The residual solvent is pulled off in vacuum. HFIP solvent can also be used with methylene chloride to aid in spinning Other methods for generating chitosan fibers are described, for example, by Sangsanoh and Supaphol, Biomacromolecules, 2006. 7(10): p. 2710-4 or Schiffman and Schauer, Biomacromolecules, 2007. 8(2): p. 594-601. The methods of the invention provide for the controlled degradation of these fibers or mats after fabrication (through the use of a buffering step).

In other embodiments, the invention provides for the production of chitosan microspheres.

Wound Healing Devices

The present invention provides wound healing devices that employ a chitosan composition. The wound healing devices may be configured by forming the chitosan composition into a shape and size sufficient to accommodate the wound being treated. If desired, the wound healing device comprises chitosan fibers. Wound healing devices are desirably produced in whatever shape and size is necessary to provide optimum treatment to the wound. These devices can be produced in forms that include, but are not limited to, plugs, meshes, strips, sutures, dressings, or any other form able to accommodate and assist in the repair of a wound. The damaged portions of the patient that may be treated with devices made of the chitosan composition of the present invention include, but are not limited to, bone, cartilage, skin, muscle and other tissues (nerve, brain, spinal cord, heart, lung). Other similar devices are administered to assist in the treatment repair and remodeling of a damaged tissue, bone, or cartilage. For some applications, it is desirable for the device to be incorporated into an existing tissue to facilitate wound repair. For other applications, it is desirable for the device to degrade over the course of days, weeks, or months. Such degradation may be advantageously tailored to suit the needs of a particular subject using the methods described herein. The elution and/or degradation profile of a chitosan composition (e.g., film, sponge) can be altered as described herein by modulating the following variables: degree of deacetylation, neutralization solution, solvent make-up, and chitosan weight %, molecular weight, and/or crystallinity. In other embodiments, a buffering step is included in the methods of producing a chitosan composition.

Crystallinity indicates the degree of structural order in a compound. Polymers such as chitosan are either amorphous or semicrystalline. Chitosan's crystallinity, like other polymers, depends on its type, number, and regularity of polymer-chain, side group chemistry, the degree of matrix packing or density, and crosslinking. The crystallinity of chitosan or its products can be controlled or altered during manufacture through its molecular weight, degree of deacetylation, and crosslinking to affect thermal properties, such as melting point, and physical-mechanical properties, such as tensile strength, Young's modulus, swelling and degradation.

Crosslinking is the process which links polymer chains together. In chitosan, crosslinking induces a three-dimensional matrix of interconnected, linear, polymeric chains. The degree or extent of crosslinking depends on the crosslinking agent. Exemplary crosslinking agents include sodium tripolyphosphate, ethylene glycol diglycidyl ether, ethylene oxide, glutaraldehyde, epichlorohydrin, diisocyanate, and genipin. Crosslinking can also be accomplished using microwave or ultraviolet exposure.

Chitosan's properties can also be altered by modulating the degree of deacetylation. In one embodiment, the degree of deacetylation is adjusted between about 50-100%, wherein the bottom of the range is any integer between 50 and 99, and the top of the range is any integer between 51% and 100%. In particular embodiments, the degree of deacetylation is 51%, 55%, 60%, 61%, 65%, 70%, 71%, 73%, 74%, 75%, 76%, 77%, 78%, 79%, 80%, 85%, 90%, and 95%. In general, the higher the degree of deacetylation, the slower the degradation of the chitosan composition.

If desired, chitosan is neutralized after acid treatment. Any base known in the art (e.g., NaOH, KOH, $NH_4OH$, $Ca(OH)_2$, $Mg(OH)_2$, or combinations thereof) may be used to neutralize an acid-treated chitosan composition. Preferably, a neutralization solution has a pH greater than 7.4 (e.g., 7.8, 8.0, 8.5, 9.0, 10, 11, and 12, 13, 14, 15, 16). The neutralization step is optional, and not strictly required. If desired, the chitosan is treated with water, PBS, or sterile saline following acid treatment. It may comprise 0.01-10.0M of a base (e.g., 0.01, 0.025, 0.5, 0.75, 0.1, 0.25, 0.5, 0.75, 1.0, 1.5, 2.0, 2.5, 3, 4, 5, 6, 7, 8, 9, 10 M) (e.g., NaOH).

Chitosan compositions neutralized in bases having lower molarity degrade more quickly. Chitosan compositions neutralized in bases of increased molarity degrade more slowly than those neutralized at lesser molarities. Thus, the degradation properties of chitosan can be modulated by altering the molarity of the neutralizing base.

In other embodiments, the concentration of the acidic solvent used to dissolve the chitosan is adjusted or the time period used to dissolve the chitosan is altered. For example, a 0.1%, 0.5%, 1%, 2%, 3% or 5% acid solution is used. In particular embodiments, chitosan is dissolved in acetic, citric, oxalic, propionic, ascorbic, hydrochloric, formic, salicylic and/or lactic acids, or a combination of those. In general, acidic solvents comprising increased levels of lactic acid form chitosan compositions that degrade more quickly and also have reduced strength and durability. In various embodiments, combinations of acetic and lactic acids are used. Acetic provides more strength and slower degradation. In contrast, lactic acid provides more flexibility. In one approach, the ratio of lactic to acetic acid is varied from 5:1, 4:1, 3:1, 2:1, 1:1, 1:2, 1:3, 1:4, to 1:5. In one embodiment, the blended acid solvent comprises 90%/10%, 80%/20% 75%/25%, 70%/30%, 60%/40%, 50%/50%. In still other embodiments, the chitosan weight % is altered from 0.25-10.0% (e.g., 0.1, 0.2, 0.25, 0.3, 0.4, 0.5, 1, 1.25, 1.5, 1.75, 2.0, 2.5, 3.0, 3.5, 4, 5, 6, 7, 8, 9, 10%). In one embodiment, a 1 wt % chitosan solution is preferred, where a 1 wt % chitosan solution contains 1 gram of chitosan per 100 ml solution. Typically, the higher the wt %, the slower the degradation.

If desired the chitosan composition is loaded with agents and the chitosan composition is delivered to a wound to form a delivery system for the agent. Preferably, the chitosan composition contains an effective amount of a chemical or pharmaceutically active component. In one embodiment, the chitosan composition self-adheres to a site at which delivery is desired. In another embodiment, an adhesive or other adhering means may be applied to the outer edges of the chitosan composition to hold the composition in position during the delivery of the chemical or pharmaceutically active component. Such adherent means may be used alone or in combination with the self-adhering properties of chitosan. Chitosan compositions provide for the local administration of a desired amount of a therapeutic agent.

Other embodiments of the present invention include wound-healing devices configured and produced as biological fasteners, such as threads, sutures and woven sheets. Threads and sutures comprising various embodiments of the chitosan composition provide a biocompatible fastening and suturing function for temporarily treating and sealing an open wound. Additionally, the biological fasteners may include pharmacologically active agents that may assist in the healing and remodeling of the tissue within and around the wound. Advantageously, such fastening and suturing devices may be treated to degrade in vivo at a desired rate. In other embodiments, the chitosan composition is administered directly to an injured area. A chitosan composition of the invention is administered by sprinkling, packing, implanting, inserting or applying or by any other administration means to a site of trauma (e.g., open wound, open fracture, complex wound).

Hemostatic Chitosan Compositions

The invention further provides chitosan compositions in the form of a hemostatic matrix (e.g., hemostatic sponges). Such compositions are useful alone or may be used for the delivery of a therapeutic or prophylactic agent delineated herein. Such matrices generally comprise porous compositions formed from chitosan. In general, sponges can be formed by providing a liquid solution of chitosan capable of forming a porous three-dimensionally stable structure. In one embodiment, a chitosan solution is prepared by dissolving deacetylated chitosan in an acidic solvent. A sponge is formed by casting the solution in a mold to achieve a desired shape. The chitosan solution is then frozen and lyophilized, thereby forming a chitosan sponge. Lyophilization is conducted to reduce the liquid (e.g. water) content of the matrix to less than about 5%, 10%, 20%, 25%, 30%, 40%, 50%, 75%, 80%, 90%, 95%, or 100% by weight. If desired, a second lyophilization step is carried out. This step is strictly optional. Following one or more lyophilizations, the chitosan composition may still include some amount of water. Typically, lypholization removes at least about 70%, 75%, 80%, 90%, 95, or 100% or the original water content of the chitosan composition. Chitosan compositions that retain some moisture may be packaged in sterile foil to maintain such moisture.

In one approach, the sponge is neutralized, for example, by treatment with a basic solution, and then re-lyophilized. The sponge matrix is stabilized structurally and remains in a highly dense and compacted state until contacted with a liquid susceptible to absorption by the matrix, for example, body fluids. For medical use, the compacted or compressed sponge is sterilized using any suitable means (e.g., radiation). The device is packaged in sterile packaging for medical use. Sponge elements or other devices of the invention may also contain one or more active therapeutic agents. For example, they include agents that promote clotting (e.g., thrombin and/or fibrinogen). Alternatively or in addition, sponge elements or other devices of the invention include antibiotics and/or growth factors that promote tissue growth and healing.

A chitosan composition is incubated with a therapeutic agent such that the agent is incorporated into the chitosan. Alternatively, or in addition, the therapeutic agent may be incorporated in the chitosan composition during fabrication. This incubation is typically carried out before or during a procedure to treat a subject using methods described herein. Sponge materials of the invention will advantageously be expandable when wetted. Preferably, the sponge has the capacity to expand at least about 10%-100% (10, 20, 30, 40, 50). In other embodiments, a sponge expands by about 200% by volume when wetted to saturation with deionized water, buffer, or an agent of the invention. Preferred sponge materials achieve rapid volume expansions (e.g., when immersed in aqueous solution). Hemostatic sponges are produced in any size required for application to a wound. In one embodiment, the expanded sponge exerts compression on surrounding tissues when implanted or delivers an active agent to the implantation site and surrounding tissue. Advantageously, chitosan compositions generated with the buffering step described herein provide for the controlled degradation of hemostatic chitosan devices, as well as providing for the controlled release of hemostatic agents.

Delivery of Chitosan Compositions

Chitosan compositions can be delivered by any method known to the skilled artisan. In one approach, a chitosan composition is locally delivered to a site of trauma in the form of a film or sponge. The film, sponge, or other wound management device can be configured to fit a wound of virtually any size. In another approach, the chitosan composition is surgically implanted at a site where promotion of healing and/or treatment or prevention of infection is required. If desired, the chitosan composition is loaded with one or more antibiotics or other biologically active agents by a clinician within the surgical suite where treatment is to be provided. This advantageously allows the chitosan composition to be loaded with a specific agent or combination of agents tailored to the needs of a particular patient at the point at which care is to be provided.

Screening Assays

As described herein, the present invention provides for the delivery of therapeutic or prophylactic agents to wounds in vivo. The invention is based in part on the discovery that therapeutic agents can be delivered using a chitosan composition where the agents and degradation of the composition is tailored to suit the needs of a particular patient. To identify chitosan compositions having the desired degradation and elution profiles, screening may be carried out using no more than routine methods known in the art and described herein. For example, chitosan compositions are loaded with one or more therapeutic agents and such compositions are subsequently compared to untreated control compositions to identify chitosan compositions that promote healing. In another embodiment, the degradation of a chitosan composition of the invention is assayed in vivo to identify the degree of deacetylation that corresponds to a the desired degradation profile. Any number of methods are available for carrying out screening assays to identify such compositions.

In one working example, candidate compounds are added at varying concentrations to a chitosan composition. The degree of infection or wound healing is then measured using standard methods as described herein. The degree of infection (e.g., number of bacteria) or wound healing in the presence of the compound is compared to the level measured in a control lacking the compound. A compound that enhances healing is considered useful in the invention; such a compound may be used, for example, as a therapeutic to prevent, delay, ameliorate, stabilize, or treat a disease described herein (e.g., tissue damage). In other embodiments, the compound prevents, delays, ameliorates, stabilizes, or treats a disease or disorder described herein. Such therapeutic compounds are useful in vivo.

In another approach, chitosan compositions having varying degrees of deacetylation are incubated in vivo, added to a wound, or are contacted with a composition comprising an enzyme having chitosan-degrading activity. The length of time required for chitosan degradation is then measured using standard methods as described herein. A chitosan composition having the desired degradation profile (e.g., degrading in 3 days, 5 days, 1 week, 2 weeks, 3 weeks, 1 month, 2 months, 3 months) is considered useful in the invention; such a composition may be used, for example, as a therapeutic to prevent, delay, ameliorate, stabilize, or treat a disease described herein (e.g., tissue damage). In other embodiments, the composition prevents, delays, ameliorates, stabilizes, or treats a disease or disorder described herein. Such therapeutic compositions are useful in vivo.

The present invention provides methods of treating pathogen infections (e.g., bacterial, viral, fungal), complex wounds, open fractures, trauma, and associated diseases and/or disorders or symptoms thereof which comprise administering a therapeutically effective amount of a composition comprising chitosan and a therapeutic or prophylactic agent of a formulae herein to a subject (e.g., a mammal, such as a human). Thus, one embodiment is a method of treating a subject suffering from or susceptible to an infection, trauma, wound, open fracture, or related disease or disorder that requires targeting of a therapeutic composition to a site. The method includes the step of administering to the mammal a therapeutic amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for an infection, in need of healing, having a trauma, wound, open fracture, or related disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The agents herein may be also used in the treatment of any other disorders in which it is desirable to promote healing or treat or prevent an infection.

In one embodiment, the invention provides a method of monitoring treatment progress. The method includes the step of determining a level of diagnostic marker (Marker) (e.g., wound healing parameters, number of bacterial cells, or any target delineated herein modulated by a compound herein, C-reactive protein, cytokine levels, or indicator thereof, etc.) or diagnostic measurement (e.g., screen, assay) in a subject suffering from or susceptible to an infection, disorder or symptoms thereof, in which the subject has been administered a therapeutic amount of a chitosan composition (e.g., a chitosan composition comprising a therapeutic or prophylactic agent) herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Test Compounds and Extracts

In general, therapeutic compounds suitable for delivery from a chitosan composition are known in the art or are identified from large libraries of both natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Compounds used in screens may include known compounds (for example, known therapeutics used for other diseases or disorders). Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds.

Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

Libraries of compounds may be presented in solution (e.g., Houghten, Biotechniques 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222: 301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is identified as containing a compound of interest, further fractionation of the positive lead extract is necessary to isolate chemical constituents responsible for the observed effect. Thus, the goal of the extraction, fractionation, and purification process is the careful characterization and identification of a chemical entity within the crude extract that achieves a desired biological effect. Methods of fractionation and purification of such heterogenous extracts are known in the art.

Small molecules of the invention preferably have a molecular weight below 2,000 daltons, more preferably between 300 and 1,000 daltons, and most preferably between 400 and 700 daltons. It is preferred that these small molecules are organic molecules.

Kits

The invention provides kits that include chitosan compositions. In one embodiment, the kit includes a chitosan composition containing a therapeutic or prophylactic agent that that prevents or treats infection (e.g., an antimicrobial agent) or that promotes healing (e.g., growth factor, anti-inflammatory, clot promoting agent, anti-thrombotic). In other embodiments, the kit contains a therapeutic device, such as a chitosan film useful in wound healing, chitosan sponge, hydrogel, or implant/prosthetic device comprising a chitosan composition described herein. If desired, the aforementioned chitosan compositions further comprise an agent described herein.

In some embodiments, the kit comprises a sterile container which contains a chitosan composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired a chitosan composition of the invention is provided together with instructions for using it in a prophylactic or therapeutic method described herein. The instructions will generally include information about the use of the composition for the treatment of a trauma, infection or related disease in a subject in need thereof. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Preparation of Chitosan Sponges

Chitosan sponges are prepared using the following steps:
(1) Dissolve chitosan in a weak organic acid aqueous solution.
(2) Freeze the resulting chitosan and acid solution.
(3) Lyophilize the frozen, solid chitosan solution, removing the water.
(4) Completely neutralize the resulting dehydrated, acidic chitosan "sponge" by hydrating it in an excess concentration and volume of sodium hydroxide aqueous solution. (See FIG. 1)
(5) Wash away the residual acidic and basic products using a copious amount ultrapure water.
(6) Buffer the hydrated, neutral chitosan sponge by soaking it in a 0.25M acetate buffer solution at pH 5.6 for thirty minutes.
(7) Remove excess liquid from the sponge.
(8) Freeze the resulting hydrated, buffered chitosan sponge.
(9) Lyophilize the frozen, solid chitosan sponge, removing the water.
(10) Store the finalized, buffered chitosan sponge product in a low humidity environment.

Sponges having a desired degradation profile were obtained by dissolving 1% w/v chitosan (61% degree of deacetylation) in a 1% v/v acid solution (where the acid is a blended 3:1 ratio of lactic and acetic acid, respectively). The sponge was cast by putting 75 ml of the dissolved chitosan solution into a 10 cm diameter aluminum dish and freezing the solution at −20° C. The cast sponge was lyophilized to reduce the water content by nearly 100%. The lyophilized sponge was then hydrated in 500 ml of 0.60M sodium hydroxide for approximately 3 minutes and physically manipulating the sponge to ensure complete hydration. The chitosan sponge was then washed in copious amounts (6 L) of purified water. Sponges neutralized in sodium hydroxide and washed in distilled water are shown at FIG. 1.

To ensure the sponge was at a neutral pH, pH was measured. Such measurements can be carried out using a pH meter or pH indicator strips.

Buffer Procedure

Once the sponge is at neutral pH, the chitosan sponge is compressed to physically expel a majority of the hydration solution. The compressed sponge is then re-hydrated in 500 ml of a 0.25M, 5.6 pH acetate buffer solution in a freezable (plastic) container for 30 minutes. The 0.25M acetate buffer is made by mixing a solution of 0.25M acetic acid (~90 ml) into a solution of 0.25M sodium acetate (~910 ml) until a pH of 5.6 is obtained. The excess buffer solution is removed and the buffered chitosan sponge is frozen at −20° C. The frozen, buffered chitosan sponge is lyophilized to reduce the water content by nearly 100%. After lyophilization, the dehydrated, buffered chitosan sponge is transferred to a container which minimizes environmental humidity.

Example 2

Buffered Sponges Degrade More Completely than Unbuffered Sponges

Figure 2:
FIG. 2 shows sponge samples from a ten-day degradation study. The sponge sample on the left is representative of neutralized chitosan sponges that have not undergone the buffering step. These sponges remain mostly intact (greater than 90% remaining) over the 10 day degradation study. The sponge sample on the right (barely visible) is representative of the chitosan sponge manufactured using the buffering step. Sponges generated using a buffering step are highly swollen and degraded (between 40 and 55% remaining) over the 10 day degradation study.
Figure 3:
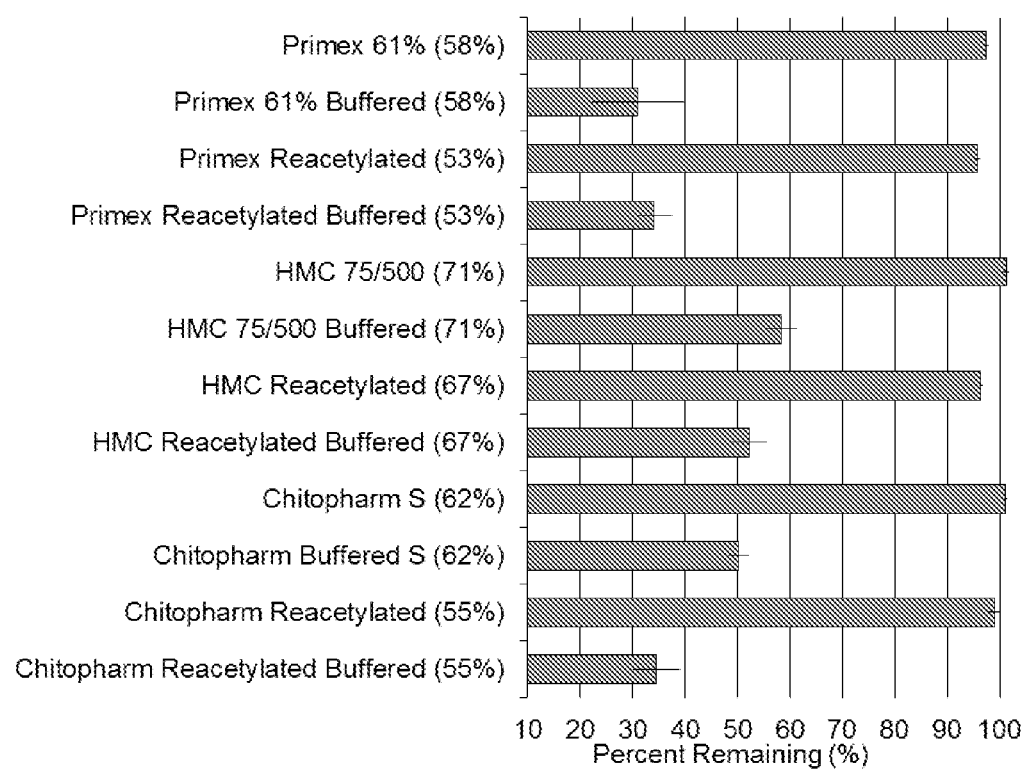
FIG. 3 is a graph that quantitates the results of a four day degradation experiment. The y-axis indicates the chitosan sponge product type, if it was buffered and its degree of deacetylation in parentheses. The x-axis indicates the average percent of the sponge that remained after 4 days of degradation in a 1 mg/ml lysozyme solution, based on the weight of the sponge in triplicate. A lower percent remaining indicates an increased degradation.

As shown in FIGS. 2 and 3, chitosan sponge's that were buffered had a significantly increased degree of degradation profile.

Sponges that have undergone a buffering step degraded more completely than unbuffered sponges. This is advantageous because as a drug delivery device for wound infection prevention or therapy, the chitosan sponge is desired to degrade away after its drug delivery task is complete (usually in 4 to 10 days). Desirably, degradation in this time frame makes a secondary, device retrieval surgery unnecessary. By eliminating residual sponge material, more complete degradation also obviates the possibility that the undegraded sponge will become a site for future infection. Thus, the buffer step solves the challenge of manufacturing a reproducibly and uniformly degradable chitosan sponge. Additionally, it allows for the degradation process to be controlled by manipulating the acid buffer type, buffer, concentration, buffer pH, and buffer soaking time (Step 6, in bold above).

In degradation studies (FIG. 2), neutralized chitosan sponges that had not undergone the buffering step remained largely intact following the 10 day degradation study. In fact, about 90% of the sponge remained after 10-days. In contrast, sponges fabricated using a buffering step degraded to a much greater degree. After 10-days of degradation, only 40-55% of the sponge remained.

The surprising efficacy of the buffering step is illustrated at FIG. 3, which shows that chitosan sponge's that were buffered had significantly increased degradation.

Example 3

Preparation of a Chitosan Composite

A composite containing chitosan sponge in chitosan gel (a "sponge-in-gel" composite) can be made from a chitosan gel component and a chitosan sponge component made as described above. A gel "matrix" component is prepared by dissolving chitosan (e.g., as described herein), filtering particulate, and allowing the solution to de-gas overnight. Chitosan solution is transferred into a container and frozen for at least 1 hour (−80° C.). The length of time the chitosan solution is frozen can be altered. After freezing, the frozen samples are lyophilized for ~48 hours and sterilized via gamma irradiation. This chitosan component is not neutralized and is used as the adhesive "gel" matrix.

A "sponge" component is prepared using the lyophilized sponges (e.g., as described herein). The lyophilized sponges are neutralized by submerging in sodium hydroxide solution (various concentrations of NaOH may be used). Hydrated sponges are rinsed with water several times before re-freezing for at least 1 hour (−80° C.). At this point in the process, the sponge may be buffered by soaking it in a 0.25M acetate buffer solution at pH 5.6 for thirty minutes. The sponge is then frozen and lyophilized for 36-48 hours. The duration of lyophilization is dependent on lyophilizer and the size of sponge. The "double" lyophilized sponge samples are sterilized via gamma irradiation.

To prepare the "sponge-in-gel" composite, a combination of "gel matrix" and "sponge" components are ground, the degree to which may be adapted from course to fine (e.g., in a standard coffee grinder). The finer components are the single-lyophilized sponge pieces, and the larger components are the double lyophilized sponge pieces. In one embodiment, at least about 25%-95% of the composite is hydrogel component. In another embodiment, at least about 5%-75% of the composite is sponge. The composite is customized based on the adhesiveness required and/or the size of the wound. An increased amount of adhesiveness is desired if the wound is prone to drainage or has increased surface area.

In another embodiment, an increased amount of sponge material is desired for a cavity wound. This blended mixture of single- and double-lyophilized chitosan sponge fragments is then hydrated with a solution (antibiotic, saline, antifungal, etc) to form a paste mixture. The resulting paste has a binding "gel" matrix (single-lyophilized sponge component) with larger, dispersed "sponge" fragments throughout the gel (double-lyophilized sponge component). The "sponge-in-gel" composite can be prepared in a short amount of time. In one embodiment, the paste is mixed and is delivered at the point-of-care. The agent is incorporated at the time the composite is hydrated. In one embodiment, the composite is delivered to a site of trauma via a sterile syringe.

Advantageously, the composite provides for a complete void fill and prevents migration of the chitosan composition within the wound. This facilitates localized delivery of an agent to the site of trauma. The "gel matrix" typically has greater adherence properties than the sponge portion of the composite. Thus, the amount of "gel matrix" can be increased or decreased based on the needs of the patient. In one embodiment, an increased amount of gel matrix (e.g., greater than about 50%, 70%, 80%, 90%, 95%) is used to increase tissue adherence. In another embodiment, an increase amount of sponge fragments (e.g., greater than about 50%, 70%, 80%, 90%, 95%) to provide for sustained elution of an agent over time. Preferably, the composite provides for the bimodal delivery of an agent. In the first phase, an agent is quickly released from the gel matrix. This first phase of elution typically occurs over the course of hours (e.g., 1, 2, 3, 4, 5, 6 or 12 hours) or days (e.g., 1, 2, 3 days). The second phase of the biomodal elution involves the sustained release of an agent from the sponge portion of the composite. This phase typically occurs over the course of days, or weeks. Desirably, the composite provides for sustained elution of an agent during the course of the composite's degradation. In one embodiment, the composite comprises a non-neutralized gel portion. In another embodiment, the composite comprises a neutralized sponge portion.

The characteristics of chitosan compositions of the invention can be assayed as follows.

Sponge Elution Tests

Sponges are subjected to elution tests by re-hydrating sponges made as described herein above in an aqueous therapeutic agent (e.g., 10 ml of 5 mg/ml amikacin and vancomycin) solution to "load" the sponge with the therapeutic agent. Once loaded with the therapeutic agent, the sponges made are submerged in 20 ml of 1× Phosphate Buffered Saline (PBS), and kept in a 37° C. incubator for the duration of the study. One ml aliquots are taken at 1, 3, 6, 24, 48, and 72 hours. Aliquots are tested for antibiotic concentration using a fluorescence polarization immunoassay technique (TDx, Abbott Labs, Abbott Park, Ill.) or high-pressure liquid chromatography (HPLC).

Antibiotic Activity

Drug activity of the aliquots is tested using a turbidity assay. Two different strains of bacteria may be used in this study. In one embodiment, vancomycin samples are tested against *Staphylococcus aureus* and amikacin samples are tested against both *Staphylococcus aureus* and *Pseudomonas aeruginosa*. 200 µl of each aliquot are added to 1.8 ml of Mueller-Hinton II broth combined with 20 µl of *S. aureus* inoculum. Amikacin samples (200 µl) are also added to 1.75 ml of trypticase soy broth (TSB) and 50 µl of *P. aeruginosa* inoculum. Samples are incubated for 24 hours at 37 C. Absorbance measurements are recorded after incubation at a wavelength of 530 nm (A530).

In other studies, antibiotic activity against *S. aureus* (Cowan I strain) is determined by utilizing the remaining antibiotic elution samples, in triplicate, in a turbidity assay. In this turbidity study, solution clarity after sufficient bacterial incubation with antibiotic eluates indicates bacterial inhibition due to antibiotic activity.

In triplicate, 200 µl of vancomycin and daptomycin eluates are individually added to the inoculum containing 1.75 ml of tryptic soy broth (TSB) and 25 µl of *S. aureus* in 5 ml polystyrene test tubes. Blanks containing neither *S. aureus* nor eluate samples, positive controls containing *S. aureus* without antibiotic eluates, and negative controls containing both *S. aureus* and high concentration antibiotic standards are mixed and incubated at 37° C. along with the eluate samples. After 24 hours of incubation, the tubes are vortexed and the absorbance at 530 nm of each inoculum solution is recorded using a spectrophotometer.

Antibiotic Quantitation

High-pressure liquid chromatography (HPLC) is used to quantify the uptake and elution of the antibiotics vancomycin from MP Biomedicals (Irvine, Calif.) and daptomycin from Cubist Pharmaceuticals (Lexington, Mass.). The Varian (Palo Alto, Calif.) HPLC system comprised a ProStar 240 Solvent Delivery, ProStar 410 Autosampler, and ProStar 325 UV-Vis Detector modules. Module control and data processing were performed using Varian's Galaxie Chromatography Data System (v1.8.508.1). Both HPLC separation methods are modified from previous research.

For daptomycin quantification the mobile phase consists of an HPLC grade acetonitrile and water (62:38, v/v) solution including 4 mM ammonium dihydrogen phosphate brought to a pH of 3.25 using phosphoric acid. Separation is accomplished using a Varian Microsorb-MV C8 column, 150 mm length and 4.6 mm inner diameter with a flow rate of 1 ml/min Daptomycin is detected at 232 nm with a retention time of 13.8 minutes (min) Daptomycin quantification are performed in a temperature range of 23.3±1.1° C.

For vancomycin quantification, the mobile phase consists of a HPLC grade acetonitrile and water (92:8, v/v) solution including 50 mM ammonium dihydrogen phosphate brought to a pH of 4 using phosphoric acid. Separation is accomplished using a Varian Microsorb-MV $C_{18}$ column, 150 mm length and 4.6 mm inner diameter with a flow rate of 1 ml/min Vancomycin was detected at 208 nm with a retention time of 24.4 min Vancomycin quantification is performed in a temperature range of 23.3±1.1° C.

Film Elution Tests

In one approach, samples are submerged into 15 ml amikacin solution (5 mg/ml) and allowed to hydrate for 2 minutes. Samples are then subjected to elution tests by submerging the films in 50 ml of 1× Phosphate Buffered Saline (PBS) and agitated in a 37 C incubator for the duration of the study. One ml aliquots are removed at 1, 3, 6, 24, 48, and 72 hours. Aliquots are tested for antibiotic concentration using a fluorescence polarization immunoassay technique (TDxFLx, Abbott Labs, Abbott Park, Ill.).

In another approach, lactic acid films with three different degrees of deacetylation are measured for daptomycin elution, and acetic acid films with different degrees of deacetylation are measured for vancomycin elution. The elution experiment is performed in triplicate by submerging films in 50 ml of PBS immediately following in situ antibiotic loading at 3 mg/ml of antibiotic. The elution procedure excludes PBS solution refreshment at each time point. The films are then incubated at 37° C. and 0.5 ml aliquots are removed at 1, 3, 6, 12, 24, 48, and 72 hours. The antibiotic concentrations of eluant samples are determined using HPLC to obtain an elution profile for each film/antibiotic combination.

Advantageously, lyophilizing a buffered film produces a highly porous coating on the surface.

Activity Tests

Drug activity of the aliquots is tested using a turbidity assay. Samples are tested against *Pseudomonas aeruginosa*. Samples (200 μl) are added to 1.75 ml of Trypticase Soy Broth (TSB) and 50 μl of *P. aeruginosa* inoculum. Samples are incubated for 24 hours at 37 C. Absorbance measurements at 530 nm on a spectrophotometer (BioTek).

Film Preparation

Using three chitosan degree of deacetylations and two acid solvents, six chitosan variations are evaluated. The numbers 61, 71, and 80 are used to indicate the % degree of deacetylation (DDA); the acid solvents, lactic acid and acetic acid, are abbreviated LA and HAc, respectively.

Primex ChitoClear (Iceland) chitosan powder at 61, 71, and 80% degree of deacetylation with 124, 1480, and 332 mPas viscosities, respectively, are used to create the films. A 1.5% (w/v) chitosan solution is prepared by dissolving the desired variation in either 1% (v/v) acetic or lactic acid solution, under constant stirring for 24 hours (hr). To remove insolubilities from the chitosan solution, it is filtered through 180 μm nylon, placed in a glass mold and transferred to a convection oven at 60° C. until dry. The dehydrated film was is and neutralized by placing it in a NaOH solution followed by rinsing in water. At this point, the film is buffered by soaking it in a 0.25M acetate buffer solution at pH 5.6 for thirty minutes. The buffered film is allowed to dry at 25° C.

In another approach, a chitosan solution that had been filtered through an 180 μm nylon screen was allowed to degas at 20° C. The solution is placed in a flat-bottomed glass dish at approximately 0.8 ml/cm$^2$ and the solvent was allowed to evaporate in a convection oven at 38° C. for 24 hrs. This produced a dried film which is neutralized by dipping the film in 2 M sodium hydroxide for approximately 1 sec, followed by pouring 2 L of distilled/deionized water over the film for rinsing. At this point, the film is buffered by soaking it in a 0.25M acetate buffer solution at pH 5.6 for thirty minutes. The buffered film is allowed to dry at 25° C. The neutralized films are dried on a large-pore sized nylon screen in a convection oven at 38° C. for 12 hrs.

In another approach, 2.5 grams of chitosan is dissolved into 247.5 ml of 1 (v/v) % blended acid solvent containing 75%/25% lactic to acetic acid. The mixture is stirred for 4-6 hours at max allowable speed on a stir plate. The chitosan solution is filtered to remove undissolved chitosan, and the filtrate was pipetted into a glass Petri dish, which was heated at 37° C. for 18-20 hours. The dried films are removed and neutralized in 2.0 M NaOH$^-$ solution for ~30-40 seconds. The films are rinsed with distilled water and pH changes are monitored until the rinsing water is neutral in pH. At this point, the film is buffered by soaking it in a 0.25M acetate buffer solution at pH 5.6 for thirty minutes. The buffered film is allowed to dry at 25° C. The re-hydrated films are then frozen at −80° C. freezer for 1 hour and then lyophilized for 24 hours. The films are then sterilized using low-dose gamma irradiation (25-32 kGy).

Uptake Studies

An uptake study is performed to determine the quantity of antibiotic solution that each chitosan composition could absorb. Antibiotic uptake determines the ability of a chitosan composition to absorb antibiotics. This study determines the concentration of antibiotic that each composition could absorb during 1 minute of rehydration. In one embodiment, a 1 mg/ml vancomycin or daptomycin phosphate-buffered saline (PBS) solution is created. Using six replications, films of known weights are submerged in 50 ml of the antibiotic solution for 1 min, where 1 min is representative of effective operating room usage. The composition is then submerged in the antibiotic solution for thirty seconds and removed. The remaining solution is tested using a high pressure liquid chromatography (Varian, Calif.) method to determine the antibiotic concentration.

This method of antibacterial loading is defined as in situ loading, as opposed to pre-loading, where antibiotics would be incorporated in the chitosan solution during film creation. After 1 minute the film is removed and a sample of remaining antibiotic solution is used in HPLC to determine its concentration. Antibiotic uptake is normalized by film weight and determined using the following relations: Antibiotic uptake=[(Initial antibiotic solution concentration−Final antibiotic solution concentration)×Antibiotic solution volume](mg)/(Chitosan film weight) (mg).

Swelling Ratio.

The swelling ratio of the chitosan composition is determined after 1 min submergence in the presence and absence of daptomycin and vancomycin solutions. In order to quantify swelling ratio, the initial volume of chitosan films is determined using electronic digital calipers accurate 0.03 mm within a range of 0 to 150 mm. The final volume is determined immediately after the antibiotic uptake procedure is performed. This data allowed the swelling ratio after 1 minute to be determined using the following relationship: Swelling ratio (%)=(Final film volume−Initial film volume)/(Initial film volume)×100

Absorbed antibiotic quantity was determined using differences in concentrations. Concurrent with the uptake study, film dimensions are measured using digital calipers in order to calculate film volume differences, yielding the swelling ratio. Chitosan film swelling ratio quantified the increase in volume as the film rehydrated.

Ultimate Tensile Strength, Young's Modulus

Neutralized chitosan compositions are subjected to tensile testing using a Universal Materials Testing Machine (Instron, Norwood, Mass.). Ultimate Tensile Strength (UTS) and Young's Modulus determines the strength and elasticity of dry/dehydrated chitosan chitosan compositions. Using six replications, chitosan compositions are punched out into ASTM E8 tensile testing specimens with an initial 25 mm-gage length and 175 mm$^2$ area. In some analyses, test specimens are cut uniformly with gauge lengths and widths of 12.7 mm and 3.5 mm respectively. Using an Instron 33R, model 4465 (Norwood, Mass.) Universal Testing Machine with a 50 N load cell automated by Instron's Bluehill 2 (v2.13) software, the ultimate tensile strength (UTS) and Young's modulus of dehydrated films were determined. Due to the necessity of controlling the test specimen's precise dimensions, it is necessary to perform this test using dehydrated chitosan film samples. The test specimen is securely placed in the hydraulic grips and tested in tension at a rate of 1 mm/min with data recorded at 200 ms intervals. The testing device software is configured to output UTS, Young's modulus and the breaking point % of elongation.

Adhesive Strength

Adhesive strength measurement investigates the adhesive strength of wet/rehydrated chitosan compositions (e.g., films) to implant grade alloy fixtures, either 316L stainless steel (ASTM F138) or 6-4 titanium (ASTM F136), using a modified ASTM standard (D5179-02). These fixtures are gripped by a universal testing machine which measures the strength required to pull the implant alloys apart. All experiments are performed with n≥5.

To determine adhesive strength, six specimen replications from all chitosan film variations are cut into minimal 38×38 mm squares Films are then submerged in 50 ml of PBS solution for 1 min, in order to simulate the in situ loading procedure, and are then positioned between cylindrical fixtures with a diameter of 35.1 mm to facilitate the adhesion test. The adhesion testing is modeled from ASTM D5179-02 in order to be performed in-house. Both Instron Universal Testing Machine hydraulic grips were made to hold either 316L SS (ASTM F138) or Ti (Ti-6Al-4V, ASTM 136) alloy fixtures. The mechanical fixture surfaces which faced each other were smoothed by superfinishing to a roughness, $R_a$, value of 0.025 μm. The superfinishing on the testing cylinders is used to provide comparison testing, not to replicate typical implant surfaces. The rehydrated chitosan films are sandwiched between the two mechanical fixtures with an automatic compression pre-load of 15 N. Immediately after reaching the pre-load force, the movable crossheads are reversed at 50 mm/min with data recorded at 30 millisecond intervals. Film thickness varied at 0.18±0 8 mm and the software gave data output in maximal force (N) which is converted into adhesive strength (kPa). Tukey's HSD statistical analysis is performed with α=0.05 to determine statistical differences between film variations.

Chitosan Degradation.

A modified procedure (Tomihata and Ikada, 1997) is used to quantify the antibiotic effect on chitosan degradation. In situ loaded and non-loaded chitosan films groups—the same groups used in the antibiotic elution and activity experiments with additional non-loaded groups yielded a total of 12 experimental groups to be tested with five replicates each—are subjected to degradation testing. The weight of clean 90 mm diameter Petri dishes and dehydrated chitosan films is established. Films marked for in situ loading are submerged in 50 ml of a standard antibiotic solution and then all films are submerged in 25 ml of 100 μg/ml 2× crystallized, chicken egg white lysozyme (MP Biomedicals) PBS solution. The samples are incubated for 20 hours at 37° C. in a convection incubator. After the incubation period, the lysozyme solution is removed and the films are dehydrated using the same method with the convection oven. The lysozyme/PBS solution is replaced and film weights are measured every 20 hours for a total of 100 hours. The new film weights are measured, which enabled degradation to be expresseed as the percent of the film that remained. The percent of the film that remained was determined using the following relationship: Percent Remaining (%)=(Petri dish and film weight at x hours−Petri dish weight) (mg)/(Petri dish and initial film weight−Petri dish weight) (mg)×100.

Statistical Analysis

Data is reported as the mean±standard deviation. One-way ANOVA was used to analyze for statistically significant differences. If statistically significant differences are found, then each pair of variations were compared using the Student t-test. Differences between chitosan composition properties are determined using the Student t-test with Bonfferoni correction. Two-way ANOVA is used to identify differences between independent variables. Analysis is performed using JMP 7.0.1 (Cary, N. Dak.). Statistical significance occurs when p<0.05. Tukey's "honest significant difference" (HSD) could also be used.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

This application includes subject matter that may be related to subject matter described in U.S. Provisional Application Nos. 61/160,539, 61/171,805, and 61/227,606, as well as U.S. Utility application Ser. No. 13/256,585; the entire contents of each of which are incorporated herein by this reference.

All patents and publications mentioned in this specification are herein incorporated by reference to the same extent as if each independent patent and publication was specifically and individually indicated to be incorporated by reference.

What is claimed is:

1. A method for producing a biodegradable chitosan film or sponge, the method comprising
    (a) dissolving chitosan in a 3:1 ratio of lactic and acetic acid solution;
    (b) forming the chitosan into a desired shape and lyophilizing the chitosan to form a dehydrated acidic chitosan composition;
    (c) neutralizing the dehydrated, acidic chitosan composition by hydrating it in an aqueous sodium hydroxide solution;
    (d) washing the chitosan composition in water to remove residual acidic and basic products;
    (e) soaking the chitosan composition in an acetate buffer solution for about thirty minutes; and
    (f) freezing and lyophilizing the chitosan film or sponge.

2. The method of claim 1, wherein the buffer has a pH between 5 and 6.

3. The method of claim 1, wherein the chitosan film or sponge is dissolved in the acid solution for a time selected from the group consisting of 1, 3, 5, 10, 15, 30, 45, 60 minutes, 3, 5, 10, and 12 hours.

4. The method of claim 1, wherein the acid solution has a concentration between about 0.05 and 2.0 molar.

5. The method of claim 1, wherein a 0.25 M acetate buffer is used.

6. The method of claim 1, wherein the chitosan film or sponge degrades by at least about 20%, 30%, 40%, 50%, 60% or more in vivo in about 10-days.

7. The method of claim 1, further comprising (g) incorporating an effective amount of at least one anti-bacterial, anti-viral, or anti-fungal agent into the chitosan composition at a point of care.

8. The method of claim 1, wherein the chitosan film or sponge is a wound management device.

9. The method of claim 7, wherein the agent is an antimicrobial.

10. The method of claim 1, wherein at least about 30, 40, 50 or 60% of the chitosan film or sponge biodegrades over at least about three-five days when implanted in a subject.

11. A chitosan film or sponge produced by the method of claim 1.

12. A wound management device comprising a chitosan film or sponge produced by the method of claim 1.

13. The wound management device of claim 12, wherein the chitosan film or sponge comprises an effective amount of an anti-bacterial, anti-viral, or anti-fungal agent.

14. The wound management device of claim 13, wherein the agent is an antibiotic selected from the group consisting of daptomycin, vancomycin, and amikacin.

15. A method for treating an infection caused by *Pseudomonas aeruginosa* or *S. aureus* in a subject at a site of trauma, the method comprising contacting the site with the wound management device of claim 12.

16. A kit comprising the wound management device of claim 12.

17. A method for treating an infection with a Gram positive bacteria, the method comprising contacting the site with the wound management device of claim 12.

* * * * *